United States Patent [19]

Kracauer, deceased et al.

[11] 4,206,209

[45] Jun. 3, 1980

[54] SUBLINGUAL ASPIRIN TABLET

[76] Inventors: Paul Kracauer, deceased, late of New York, N.Y.; by Gertrude Kracauer, exectrix, 210 W. 90th St., New York, N.Y. 10024

[21] Appl. No.: 957,323

[22] Filed: Nov. 2, 1978

[51] Int. Cl.$^2$ ...................... A61K 31/60; A61K 31/61
[52] U.S. Cl. ...................................... 424/234; 424/230
[58] Field of Search ................................ 424/230–234

[56] References Cited

U.S. PATENT DOCUMENTS 2,801,951  8/1957  Cooper, Jr. ........................... 424/330

Primary Examiner—Stanley J. Friedman
Attorney, Agent, or Firm—Sherman & Shalloway

[57] ABSTRACT

Aspirin is the most commonly used antipyretic, analgesic, anti-inflammatory agent. The usual pain-relieving adult dosage is 300 to 600 mg.

To minimize frequent aspirin-induced gastric disturbance, many aspirin products contain buffering agents. Only a portion of the aspirin acts as aspirin, as part of the aspirin is decomposed into salicylic acid and acetic acid. Buffering agents cannot fully neutralize these acids along with the gastric acids, especially when larger aspirin doses are required. The likelihood of G I tolerance cannot be fully improved by any buffering agent.

Aspirin is effective within 15 to 25 minutes after swallowing.

1 Claim, No Drawings

SUBLINGUAL ASPIRIN TABLET

The primary objects of my invention are: Faster action, no stomach irritation, convenient ingestion, full benefit of the aspirin by preventing decomposition.

The objects of my invention have been achieved by making it possible to ingest the aspirin sublingually by means of a tablet formulated to be practically tasteless, which dissolves rapidly, uniformly, and completely under the tongue. It is absorbed without being decomposed, it is not irritation, it goes immediately into the blood stream, and it produces no stomach disturbance. Furthermore it's action is super-fast: it is effective within 3 to 5 minutes.

The harmless, edible inert ingredients added to the aspirin in very small amounts and proper proportions stabilize the aspirin, neutralize the taste, minimize any possible irritation, and make the tablet porous to effect fast solubility and absorbtion by the blood vessels under the tongue without decomposition of the aspirin.

DESCRIPTION OF THE INVENTION

This invention is concerned with a novel, practical method of ingesting an aspirin tablet; such a tablet is to be placed under the tongue.

The purpose of this method is: faster action, faster relief of pain, elimination of the necessity to use water or other liquid for swallowing, and avoidance of gastric disturbance; the prevention of aspirin decomposition into Acetic Acid and Salicylic Acid in the stomach. The sublingual tablet enters the bloodstream directly.

Obviously, such a tablet, when placed under the tongue, must dissolve completely and rapidly without objectionable taste or irritation. These and other objects of the present invention have been accomplished by adding to the Aspirin several components which neutralize the Aspirin taste, effect the absorbtion by the blood vessels under the tongue, and give the compressed tablet a certain porosity. None of the ingredients used chemically decomposes the Aspirin.

This has all been achieved in such a way that the complete mixture of Aspirin plus the other components is directly compressible by means of the conventional manufacturing procedures.

The single components of my invention are: Granulated Sugar, Mannitol, Sodium Citrate anhydrous, Calcium Glycero Phosphate, Mineral Oil, a non-ionic hydrophilic surfactant, a non-ionic lipophilic surfactant, and Glycerine.

Granulated Sugar is the excipient; Mannitol, Sodium Citrate anhydrous, and Calcium Glycero Phosphate are the taste neutralizers. Mineral Oil, Glycerine, and the two surfactants are the components which effect the vitally essential rapid dissolving of the tablet under the tongue by making the tablet porous; whereby even the smallest amount of saliva forms an emulsion effecting fast and uniform tablet dissolution and improving the desired absorbability of the tablet.

All the ingredients are compatible with one another. The very easily decomposable Aspirin remains undecomposed. Sodium Citrate anhydrous enhances the absorbability of Aspirin. The Mannitol in conjunction with the smallest amount of a Calcium compound, i.e. Calcium Glycero Phosphate, is the primary taste neutralizer.

Sugar, being a stabilizer of Aspirin, enters the blood stream together with all the other components, thereby enhancing uniform absorbtion under the tongue.

The amounts and the proportions of each of the components of my invention are critical in the achievement of the objects of this invention. The optimum amounts of each component of my invention are:

| | |
|---|---|
| Aspirin | 100 parts |
| Granulated Sugar | 150 to 180 parts |
| Mannitol | 10 to 18 parts |
| Sodium Citrate anhydrous | 3 to 4 parts |
| Calcium Glycero Phosphate | 1 to 2 parts |
| Mineral Oil | 3 to 5 parts |
| Glycerine | 1 to 1.5 parts |
| Non-ionic lipophilic surfactant | .3 to .4 parts |
| Non-ionic hydrophilic | |

The characteristics of the present invention will be further understood by reference to the following examples.

EXAMPLES

The following examples illustrate the invention, but do not limit the invention.

EXAMPLE 1

| | | |
|---|---|---|
| Part A: | Blend uniformly together - | |
| | Aspirin (40 mesh) | 300 g |
| | Mannitol | 20 g |
| | Sodium Citrate anhydrous | 10 g |
| | Calcium Glycero Phosphate | 3 g |
| Part B: | Blend uniformly together - | |
| | Granulated Sugar | 550 g |
| | Mineral Oil | 12 g |
| | Glycerine | 3 g |
| | Non-ionic hydrophilic surfactant | 1 g |
| | Non-ionic lipophilic surfactant | 1 g |
| | | 900 g |

Blend Part A with Part B and compress directly with medium pressure to make 1000 tablets, each weighing 0.9 g and each containing 0.3 g Aspirin.

EXAMPLE 2

| | | |
|---|---|---|
| Part A: | Blend together - | |
| | Aspirin (40 mesh) | 330 g |
| | Granulated Sugar | 530 g |
| | Mannitol | 25 g |
| | Sodium Citrate anhydrous | 12 g |
| | Calcium Glycero Phosphate | 3 g |
| Part B: | Make a mixture of - | |
| | Mineral Oil | 15 g |
| | Glycerine | 4 g |
| | Non-ionic hydrophilic surfactant | 1 g |
| | Non-ionic lipophilic surfactant | 921 g |

Blend Part B with Part A and press directly with medium pressure to make 1000 tablets, each weighing 0.921 g and each containing 0.33 g Aspirin.
Preferred Non-ionic hydrophilic surfactant: Polysorbate 80.
Preferred Non-ionic lipophilic surfactant: Atmos 300

I claim:
1. A sublingual rapidly soluble practically tasteless, non-irritating and stable aspirin tablet comprising:

| | |
|---|---|
| Aspirin | 100 parts |
| Granulated Sugar | 150 to 180 parts |
| Mannitol | 10 to 18 parts |
| Sodium Citrate Anhydrous | 3 to 4 parts |
| Calcium Glycerophosphate | 1 to 2 parts |
| Mineral Oil | 3 to 5 parts |

| -continued | |
|---|---|
| Glycerine | 1 to 1.5 parts |
| Non-ionic lipophilic surfactant | .3 to .4 parts |
| Non-ionic hydrophilic surfactant | .3 to .4 parts | wherein all parts are by weight, said non-ionic hydrophilic surfactant having an HLB of from 15 to 17 and said non-ionic lipophilic surfactant having an HLB of from 2 to 5.

* * * * *